United States Patent [19]
Shiotani et al.

[11] Patent Number: 5,292,860
[45] Date of Patent: Mar. 8, 1994

[54] COPOLYMER AND METHOD FOR PRODUCTION THEREOF

[75] Inventors: Takeshi Shiotani, Kakogawa; Genta Kobayashi, Takasago, both of Japan

[73] Assignee: Kanegafuchi Kagaku Kogyo Kabushiki Kaisha, Osaka, Japan

[21] Appl. No.: 945,505

[22] Filed: Sep. 16, 1992

[30] Foreign Application Priority Data

Sep. 17, 1991 [JP] Japan .................. 3-267255

[51] Int. Cl.$^5$ .................. C08G 63/06; C12D 7/62
[52] U.S. Cl. .................. 528/361; 435/41; 435/135; 435/822; 435/828; 528/354; 528/355; 528/491
[58] Field of Search ............... 528/361, 354, 355, 491; 435/135, 136, 146, 41, 822, 828; 549/550

[56] References Cited

U.S. PATENT DOCUMENTS 4,800,162 1/1989 Matson .................. 435/280
5,126,255 6/1992 Anderson et al. .................. 435/135
5,138,029 8/1992 Nishioka et al. .................. 528/354

OTHER PUBLICATIONS

Brandl et al., (1989) Int. J. Biol. Macromol. 11:49-55.

Primary Examiner—John Kight, III
Assistant Examiner—Shelley A. Dodson
Attorney, Agent, or Firm—Birch, Stewart, Kolasch & Birch

[57] ABSTRACT

The present invention is directed to a copolymer containing a 3-hydroxybutyrate (3HB) unit and a 3-hydroxyhexanoate (3HHx) unit, a three-component copolymer containing at least a 3-hydroxybutyrate (3HB) unit and a 3-hydroxyhexanoate (3HHx) unit, and a four-component copolymer containing at least a 3-hydroxybutyrate (3HB) unit and a 3-hydroxyhexanoate (3HHx) unit. The use of a microorganism of the genus Aeromonas according to the present invention makes it possible to produce a wide variety of plastic materials ranging from rigid plastics to elastic plastics by selecting copolymer components and adjusting their composition.

22 Claims, 3 Drawing Sheets

COPOLYMER AND METHOD FOR PRODUCTION THEREOF

FIELD OF THE INVENTION

The present invention relates to a novel copolymer polyester, a method for production thereof a and a microorganism used therefor, more specifically to a plastic-like polymer which undergoes microbial degradation in natural environments such as soil, rivers and seas, and a method for production thereof.

BACKGROUND OF THE INVENTION

A large number of microorganisms have been found to accumulate polyesters, as energy storage compounds, in the cells thereof. A typical example thereof is poly-3-hydroxybutyrate [hereinafter simply referred to as P(3HB)], which is a homopolymer containing a monomer unit (3HB) represented by the following Formula:

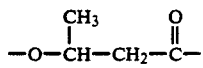

3HB

P(3HB) is a so-called biodegradable plastic, which undergoes biological degradation in natural environments; however, when viewed as a polymer material, it is insufficient for practical use because it is highly crystalline, hard and brittle.

As a means for overcoming these drawbacks, it has been proposed to incorporate a monomer unit which is structurally different from 3HB to compose the polyester. The methods based on this concept can be roughly divided into two groups as follows.

(1) According to Japanese Patent Laid-Open Nos. 150393/1982, 69225/1983, 269989/1988, 48821/1989 and 156320/1989, copolymer P(3HB-CO-3HV), containing 3-hydroxyvalerate (simply referred to as 3HV) and 3HB, is obtained by culturing *Alcaligenes eutrophus*, a microorganism which essentially produces P(3HB), from a carboxylic acid having an odd number of carbon atoms, such as propionic acid or valeric acid, as a carbon source. Similarly, it is reported that copolymer P(3HB-CO-4HB), containing 4-hydroxybutyrate (simply referred to as 4HB) and 3HB, is obtained from 4-hydroxybutyric acid or γ-butyrolactone, as a carbon source.

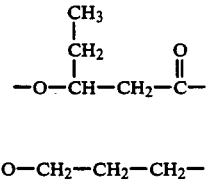

(2) According to Japanese Patent Laid-Open No. 226291/1988, it is reported that copolymer P(3HA), having 3-hydroxyalkanoate (simply referred to as 3HA) having 6 to 12 carbon atoms can be biosynthesized by *Pseudomonas oleovorans* ATCC29347, a hydrocarbon-utilizing bacterium, from alkanes as a carbon source. Here, to provide a clear representation of the relationship between each monomer unit structure and carbon number in 3HA, this monomer unit is referred to as a $C_x$ unit.

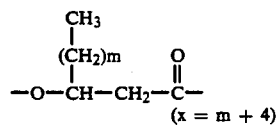

$$(x = m + 4)$$

According to the above-mentioned patent publications, 3HB is a $C_4$ unit and 3HV is a $C_5$ unit; *Pseudomonas oleovorans* is capable of intracellularly synthesizing and accumulating copolymers containing $C_6$ to $C_{12}$ units.

Also, "Applied and Environmental Microbiology, 1988, pages 1977–1982" states that the carbon source alkanes should have at least 6 carbon atoms in order for *Pseudomonas oleovorans* to synthesize a polyester, and that units exceeding $C_{12}$ is not synthesized even if an alkane having a carbon number of 12 or more are added.

As stated above, two types of copolymer have been proposed. The copolymers described in (1) have a small number of methylene groups in the side chain thereof, and they are physically plastic-like polymers. The copolymers described in (2) have a large number of methylene groups in the side chain thereof, and they are physically gel-like polymers. However, with respect to the copolymers described in (1) above, the costs of cultivation are inevitably high because starting materials for 3HV, 4HB and other copolymer components must be separately added, in addition to the major carbon source as a starting material for 3HB. For this reason, the discovery of strains which synthesize copolymers from cheap starting materials and the establishment of conditions for their culture have been of concern.

The present inventors have conducted investigations in a search for microorganisms which utilize long-chain fatty acids and naturally occurring oils and fats to biologically synthesize and accumulate a polyester in the cells thereof, and have found strains which accumulate plastic-like two- to four-component copolymers described in (1) above having a small number of methylene groups in the side chain thereof. The present inventors have made further investigations based on this finding, and thus developed the present invention.

SUMMARY OF THE INVENTION

An object of the present invention is to provide a novel copolymer which is a biodegradable plastic which undergoes enzymatic degradation by depolymerases, lipase and other enzymes in the natural environment, the copolymer containing at least a 3-hydroxybutyrate (3HB) unit and a 3-hydroxyhexanoate (3HHx) unit.

Another object of the present invention is to provide *Aeromonas cavaie* capable of synthesizing the copolymer.

A further object of the present invention is to provide a method for production of the copolymer using a microorganism of the genus Aeromonas.

Accordingly, the microbial strains discovered by the present inventors are the FA-440 strain, which grows in the presence of oleic acid as the only carbon source and synthesizes polyester, and the OL-338 strain, which grows in the presence of triolein (olive oil) as the only carbon source and synthesizes polyester. Analyses for monomer units of the copolymers synthesized by fermentation using these strains revealed the presence of the 3HB unit and the 3-hydroxyhexanoate (3HHx) unit, and NMR analyses revealed that the copolymer P(3HB-CO-3HHx) can be obtained.

These two strains were identified as *Aeromonas caviae* and *Aeromonas hydrophila*, strain FA-440 and strain OL-338, respectively.

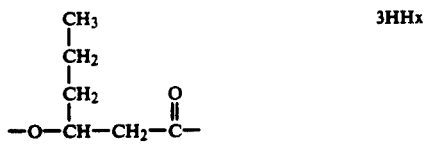

The present invention is based on the discovery of these microorganisms.

Accordingly, the present invention essentially relates to:

(1) a copolymer containing 50 mol % to 98 mol % of a 3-hydroxybutyrate (3HB) unit and 50 mol % to 2 mol % of a 3-hydroxyhexanoate (3HHx) unit;

(2) a three-component copolymer containing at least a 3-hydroxybutyrate (3HB) unit and a 3-hydroxyhexanoate (3HHx) unit, wherein the third component is, for example, one unit selected from the group consisting of a 4-hydroxybutyrate (4HB) unit, a 3-hydroxyvalerate (3HV) unit and a 3-hydroxypropionate (3HP) unit;

(3) a four-component copolymer containing at least a 3-hydroxybutyrate (3HB) unit and a 3-hydroxyhexanoate (3HHx) unit, wherein the third component and the fourth component are, for example, two units selected from the group consisting of a 4-hydroxybutyrate (4HB) unit, a 3-hydroxyvalerate (3HV) unit and a 3-hydroxypropionate (3HP) unit;

(4) *Aeromonas caviae* capable of synthesizing the copolymer described in any one of (1) to (3) above; and (5) a method for production of the copolymer described in any one of (1) to (3) above using a microorganism of the genus Aeromonas. More specifically, it relates to:

1) a method for production of a copolymer containing a 3-hydroxybutyrate (3HB) unit and a 3-hydroxyhexanoate (3HHx) unit, wherein a microorganism of the genus Aeromonas is cultured with limitation of nutrients except for carbon sources, using as carbon sources a fatty acid having an even number of not less than 6 carbon atoms, a lower alcohol ester thereof or a naturally occurring oil or fat;

2) a method for production of a copolymer containing at least one unit selected from the group consisting of a 3-hydroxypropionate (3HP) unit, a 3-hydroxyvalerate (3HV) unit and a 4-hydroxybutyrate (4HB) unit, wherein a microorganism of the genus Aeromonas is cultured with limitation of nutrients except for carbon sources, using as carbon sources 5-chlorovaleric acid or propionic acid, a fatty acid having an odd number of not less than 5 carbon atoms, 4-hydroxybutyric acid or γ-butyrolactone;

3) a method for production of a three-component copolymer containing at least a 3-hydroxybutyrate (3HB) unit, a 3-hydroxyhexanoate (3HHx) unit and one unit selected from the group consisting of 1) a 3-hydroxypropionate (3HP) unit, 2) a 3-hydroxyvalerate (3HV) unit and 3) a 4-hydroxybutyrate (4HB) unit, which units correspond to the following respective carbon sources, wherein a microorganism of the genus Aeromonas is cultured with limitation of nutrients except for carbon sources, using as carbon sources a fatty acid having an even number of not less than 6 carbon atoms, a lower alcohol ester thereof, or a naturally occurring oil or fat, and 1) 5-chlorovaleric acid or propionic acid, 2) a fatty acid having an odd number of not less than 5 carbon atoms or 3) 4-hydroxybutyric acid or γ-butyrolactone; and 4) a method for production of a four-component copolymer containing at least a 3-hydroxybutyrate (3HB) unit, a 3-hydroxyhexanoate (3HHx) unit and two units selected from the group consisting of 1) a 3-hydroxypropionate (3HP) unit, 2) a 3-hydroxyvalerate (3HV) unit and 3) a 4-hydroxybutyrate (4HB) unit, which units correspond to the following respective carbon sources, wherein a microorganism of the genus Aeromonas is cultured with limitation of nutrients except for carbon sources, using as carbon sources a fatty acid having an even number of not less than 6 carbon atoms, a lower alcohol ester thereof, or a naturally occurring oil or fat, and two carbon sources selected from the group consisting of 1) 5-chlorovaleric acid or propionic acid, 2) a fatty acid having an odd number of not less than 5 carbon atoms or 3) 4-hydroxybutyric acid or γ-butyrolactone.

DETAILED DESCRIPTION OF THE INVENTION

Figure 1:
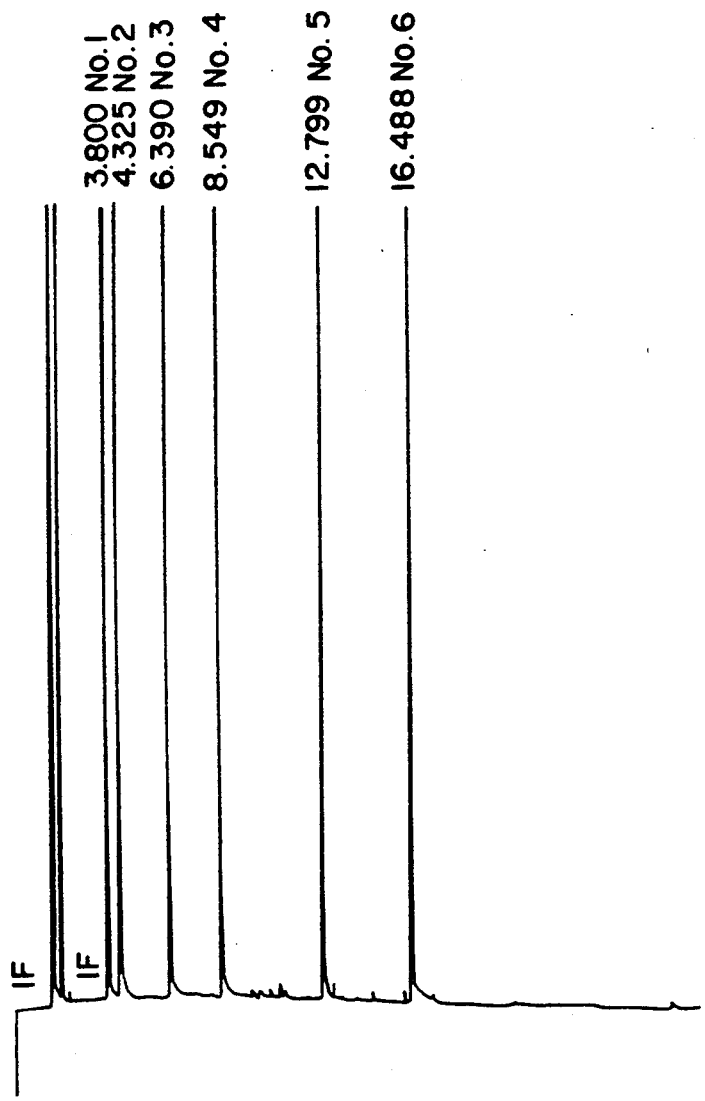
FIG. 1 shows a gas chromatogram of the methyl ester of 3-hydroxy fatty acid.

The method for production of a copolymer according to the present invention, which uses a microorganism of the genus Aeromonas, is a novel method which has not yet been conventionally reported, and although the mechanism of biosynthesis involved therein remains unknown, it has the following features, as described in Examples.

(1) When polyester is synthesized by fermentation using as a carbon source a fatty acid having an even number of not less than 6 carbon atoms, a lower alcohol ester thereof, or a long-chain fatty acid having an even number of 12 to 22 carbon atoms, which is a major constituent component of naturally occurring oils and fats, the copolymer P(3HB-CO-3HHx) containing $C_4$ and $C_6$ units can be obtained.

(2) When polyester is synthesized by fermentation using as a carbon source 5-chlorovaleric acid or propionic acid, the copolymer P(3HB-CO-3HP) containing 60 to 2 mol % of 3-hydroxypropionate (3HP) units can be obtained.

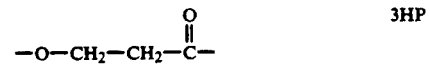

(3) When polyester is synthesized by fermentation using as a carbon source a fatty acid having an odd number of not less than 5 carbon atoms, such as valeric acid which has a carbon number of 5, the copolymer P(3HB-CO-3HV) containing not less than 90 mol % of a 3HV unit can be obtained.

(4) When polyester is synthesized by fermentation using as a carbon source 4-hydroxybutyric acid or γ- butyrolactone, the copolymer P(3HB-CO-4HB) can be obtained.

(5) When polyester is synthesized by fermentation using as a carbon source a mixture of a fatty acid having an odd-number of not less than 5 carbon atoms and a fatty acid having an even number of not less than 6 carbon atoms, the three-component copolymer containing 3HB units, 3HV units and 3HHx units can be obtained.

(6) When polyester is synthesized by fermentation using as a carbon source olive oil, valeric acid or 4-hydroxybutyric acid, the four-component copolymer containing 3HB units, 4HB units, 3HV units and a 3HHx units can be obtained.

(7) When polyester is synthesized by fermentation using as a carbon source glucose, fructose, acetic acid or butyric acid, a homopolymer of P(3HB) can be obtained. The amount of polymer is large when butyric acid is used, and the amount is small when glucose, fructose or acetic acid is used.

(8) When caproic acid or $\beta$-hydroxycaproic acid is used as a carbon source, the $C_6$ unit content can be increased.

The microorganism of the present invention is not subject to limitation, as long as it is a microorganism of the genus Aeromonas capable of synthesizing the copolymer as described above. Examples thereof include *Aeromonas caviae* and *Aeromonas hydrophila*. The bacteriological characteristics of *Aeromonas caviae*, strain FA-440, are shown in Table 1. The FA-440 strain and the OL-338 strain, found as examples of the microorganisms of the present invention, were isolated from soil at Takasago-cho Miyamae-machi, Takasago-shi, Hyogo-ken, Japan, and the FA-440 strain has been deposited under accession number FERM BP 3432.

TABLE 1

| Bacteriological Characteristics of *Aeromonas caviae* FA-440 | |
|---|---|
| Test Items | Test Results |
| Morphology | Bacillus Rods |
| Gram Stain | − |
| Spore | − |
| Motility | + |
| Flagella Number | >1 |
| Oxidase | + |
| Catalase | + |
| OF | F |
| Requirement for Na+ | − |
| Lipase | + |
| Resistant of O/129 | |
| 10 ppm | Resistant + |
| 150 ppm | Resistant + |
| Brown Water-Soluble Pigment | − |
| Growth in Nutrient Broth at 37° C. | + |
| Indole Production in 1% Peptone Water | + |
| Esculin Hydrolysis | + |
| Acetoin from Glucose (Voges-Proskauer) | − |
| Gas from Glucose | − |
| H₂S from Cysteine | − |
| NO₃⁻ Reduced to NO₂⁻ | + |
| Production of Acid | |
| Salicin | + |
| Sucrose | + |
| Glucose | + |
| Mannitol | + |
| Utilization of: | |
| L-Arabinose | + |
| Arginine | + |
| Histidine | + |
| Mannitol | + |

TABLE 1-continued

| Bacteriological Characteristics of *Aeromonas caviae* FA-440 | |
|---|---|
| Test Items | Test Results |
| GC Content of Intracellular DNA (mol %) | 62 |

Such microorganisms of the genus Aeromonas according to the present invention differ from *Alcaligenes eutrophus*, a known typical P(3HB) producer bacterium, with respect to some points of the mechanism of polyester biosynthesis.

1) The most significant difference concerns with polymerase specificity for $\beta$-hydroxyhexanyl CoA; the strains of the genus Aeromonas possess a polymerase which acts on the $\beta$-hydroxyhexanyl CoA produced in the course of the $\beta$-oxidation of fatty acids, while *Alcaligenes eutrophus* does not have it.

2) Another major difference concerns propionic acid metabolism. When fed propionic acid as a carbon source, *Alcaligenes eutrophus* synthesizes a copolymer of 3HB and 3HV (Japanese Patent Laid-Open No. 69224/1983), while the microorganisms of the genus Aeromonas produce 3HP in place of 3HV. This demonstrates that the $\beta$-ketothiolase of the microorganisms of the genus Aeromonas is incapable of dimerizing propinyl CoA and acetyl CoA. This is supported by the fact that when fed with valeric acid, they biologically synthesize not less than 90 mol % of P(3HV).

3) The dimerization of two acetyl CoA units itself is not the major action of the microorganisms of the genus Aeromonas, and polyester synthesis from $\beta$-hydroxyacyl CoA, an intermediate metabolite involved in the $\beta$-oxidation pathway, is dominant.

The present invention provides a microorganism of the genus Aeromonas having the above characteristics, a copolymer synthesized by fermentation using the microorganism, and a method for production thereof, specifically a technical means for preparing a two- to four-component plastic-like polyester copolymer containing $C_3$ through $C_6$ monomer units using a naturally abundant oil, fat or long-chain fatty acid as the major starting material.

Specifically, copolymer P(3HB-CO-3HHx) having a $C_4$(3HB):$C_6$(3HHx) ratio of 70:30 to 90:10 can be obtained simply by aerobically culturing a microorganism of the genus Aeromonas with limitation of nutrients other than carbon sources, usually nitrogen, using as a carbon source a fatty acid having an even number of not less than 6 carbon atoms, a lower alcohol ester thereof, or a naturally abundant oil or fat (vegetable oil or fish oil). For the purpose of increasing the $C_6$ unit content, caproic acid or $\beta$-hydroxycaproic acid is also added, and for the purpose of increasing the $C_4$ unit content, butyric acid or $\beta$-hydroxybutyric acid is also added.

Thus, the composition can be controlled in the $C_4$(3HB):$C_6$(3HHx) range from 50:50 to 98:2. Because the polymerase of the FA-440 and OL-338 strains is more compatible with $\beta$-hydroxybutyryl CoA than with $\beta$-hydroxyhexyl CoA, they are incapable of producing a copolymer rich in $C_6$ units.

The naturally occurring oils and fats used herein may be at least one kind selected from the group consisting of corn oil, soybean oil, safflower oil, sunflower oil, olive oil, coconut oil, palm oil, rapeseed oil, fish oil, whale oil, lard and beef tallow.

Also, P(3HB-CO-3HP) containing 40 to 60 mol % of a $C_3$(3HP) unit can be obtained by culturing a microorganism of the genus Aeromonas using 5-chlorovaleric acid or propionic acid as a carbon source. In this case as well, the $C_4$ unit content can be increased by also adding butyric acid or $\beta$-hydroxybutyric acid as a starting material for 3HB in the same manner as above. Thus, the content can be controlled in the $C_4$:$C_3$ range from 40:60 to 98:2.

When polyester is synthesized by fermentation using a fatty acid having an odd number of not less than 5 carbon atoms, such as valeric acid, which has 5 carbon atoms, P(3HB-CO-3HV) containing not less than 90 mol % of 3HV units can be obtained.

When 4-hydroxybutyric acid or $\gamma$-butyrolactone is used as a carbon source, P(3HB-CO-4HB) can be synthesized. This is the same as with *Alcaligenes eutrophus*, but the microorganisms of the genus Aeromonas tend to produce higher 3HB contents than those produced by *Alcaligenes eutrophus*, provided that they are cultured under the same conditions. When a mixture of a long-chain fatty acid and 4-hydroxybutyric acid is used as a carbon source, P(3HB-CO-3HHx-CO-4HB) can be synthesized.

On the basis of the intrinsic properties that when the carbon source is a fatty acid having an even number of not less than 6 carbon atoms, a lower alcohol ester thereof, or a naturally occurring oil or fat, the organism produces a copolymer containing two units of $C_4$ and $C_6$, and that when the carbon source is valeric acid (a $C_5$ fatty acid), the microorganism produces a polyester containing $C_5$ alone, as described above, a three-component copolymer P(3HB-CO-3HV-CO-3HHx), which is capable of freely adjusting the ratio of the ($C_4+C_6$) units and the $C_5$ unit, can be synthesized by feeding the microorganism a carbon source mixture of a fatty acid having an even number of not less than 6 carbon atoms and valeric acid (or a fatty acid having an odd number of not less than 5 carbon atoms). Also, a three-component polyester P(3HB-CO-3HP-CO-3HHx), which is capable of freely adjusting the ratio of the ($C_4+C_6$) units and the $C_3$ unit can be synthesized by feeding the microorganism propionic acid (a $C_3$ fatty acid) in place of valeric acid.

As in the case of the above-mentioned three-component copolymer, by feeding a microorganism of the genus Aeromonas a carbon source mixture comprising a fatty acid having an even number of not less than 6 carbon atoms, a lower alcohol ester thereof, or a naturally occurring oil or fat, and any two kinds selected from the group consisting of 5-chlorovaleric acid and propionic acid, a fatty acid having an odd number of not less than 5 carbon atoms, and 4-hydroxybutyric acid or $\gamma$-butyrolactone, a four-component copolymer containing a 3-hydroxybutyrate (3HB) unit, a 3-hydroxyhexanoate (3HHx) unit and any two kinds selected from the group consisting of a 3-hydroxypropionate (3HP) unit, a 3-hydroxyvalerate (3HV) unit and a 4-hydroxybutyrate (4HB) unit, which units correspond to the above-mentioned additional carbon sources, respectively, can be produced.

As stated above, in the present invention, various copolymers containing $C_3$ through $C_6$ units can be synthesized by fermentation on the basis of the intrinsic properties of the microorganisms of the genus Aeromonas.

An already reported strain which biologically synthesizes copolymers of $C_4$ through $C_6$ units is *Rhodospirillum rubrum* (Int. J. Biol. Macromol., 1989, 11, 49). Accordingly, Fuller et al. reported results of fermentation synthesis of polyesters using carboxylic acids having 2 to 10 carbon atoms as carbon sources, wherein the polyesters are copolymers containing $C_4$, $C_5$ and $C_6$ units, rather than the two-component copolymers containing basically the $C_4$ and $C_6$ units produced by microorganisms of the genus Aeromonas. Therefore, *Rhodospirillum rubrum* lacks the capability of freely adjusting the ratio of the ($C_4+C_6$) component and the $C_5$ component.

Also, *Rhodospirillum rubrum* appears to possess a mechanism of biosynthesis totally different from that of the genus Aeromonas. For example, the $C_5$ unit is produced from acetic acid or butyric acid, and the 100% pure $C_5$ unit is produced from propionic acid. The mechanism of biosynthesis in *Rhodospirillum rubrum* appears to involve no $\beta$-oxidation pathway as in the genus Aeromonas, since it synthesizes polyester under lighting and anaerobic conditions as a phototropic bacterium, and since it grows and synthesizes polyester mainly in the presence of a carboxylic acid having not more than 7 carbon atoms.

In sum, the microorganisms of the genus Aeromonas synthesize two components of $C_4$ and $C_6$ units, through $\beta$-oxidation of long-chain fatty acids, while the polyesters synthesized by *Rhodospirillum rubrum* lack regularity. Also, the problem in synthesizing a polyester using *Rhodospirillum rubrum* is the extremely low growth rate due to culturing under lighting and anaerobic conditions, as described in the paper of Fuller et al. Accordingly, a lack of practical applicability has been pointed out, wherein the polyester synthesis rate is so low that as long as 10 days are required to obtain about 0.5 g of dry cells per liter.

On the other hand, the microorganisms of the genus Aeromonas exhibit excellent productivity. For example, only two days are necessary to obtain 20 g of dry cells per liter, since they grow and synthesize polyesters under aerobic conditions.

Although the polyester synthesized by fermentation using the microorganisms of the present invention can easily be obtained by culturing the microorganism under nitrogen source limitation as known generally, the desired polyester can also be synthesized even under limitation of essential nutrients other than carbon sources, such as phosphorus, minerals and vitamins. In this case, fermentation synthesis of the polyester is usually carried out in two stages, since the growth of bacterial cells can be suppressed.

The first stage is aimed at the growth of the bacterial cells, wherein the microorganism is cultured under nutrient-rich conditions. In this case, not only fatty acids but also any carbon sources can be used optionally, as long as they can be utilized, since the bacterial cells show almost no polyester synthesis.

In the second stage, the bacterial cells grown in the first stage are washed and recovered, after which they are cultured from a newly added carbon source to synthesize the polyester. Therefore, the culturing conditions in this second stage are important. The carbon source added in the second stage is a starting material for the polyester synthesis; the structure of this carbon source determines the structure of the polyester.

Thus, the carbon source used in the present invention means the carbon source added in this second stage. As described above, by preparing various kinds of carbon sources, various kinds of copolymer containing $C_3$ to $C_6$ units can be synthesized by fermentation by using the microorganisms of the genus Aeromonas. At the same time, the nitrogen source is also limited. In this stage, the C/N ratio is preferably not less than 7; and polyester induction is possible even when the nitrogen source is not added. If the C/N ratio is less than 7, the carbon source is consumed for energy metabolism for the growth of the bacterial cells and for synthesis of bacterial cell components, which reduces the amount of carbon source used for polyester synthesis, thus considerably lowering the polyester yield.

Culturing conditions for the second stage are normally the a pH of 6 to 8, a temperature of 25° to 35° C., an air flow rate of 0.5 to 2 vvm, and a cultivation time of 24 to 48 hours.

Recovery of the copolymer accumulated in the bacterial cells can be achieved by a conventional method. For example, after completion of the cultivation, the bacterial cells are washed with distilled water, methanol, etc., and dry cells obtained by drying under reduced pressure are extracted with chloroform, etc., and then subjected to centrifugation, filtration and other procedures to remove the cells, after which methanol is added to the extract to precipitate and recover the copolymer.

Although the polyesters synthesized by fermentation using microorganisms are biodegradable plastics which decompose in the natural environment, their structures have been limited, since they are synthesized by the action of highly specific enzymes. This is based on the genetic characteristics of the microorganisms and is attributable to 1) the limited availability of the carbon sources which can be utilized by the microorganisms, and 2) the limitation on the pathways for the metabolism of the carbon source and the polyester synthesis.

In the present invention, it is possible to synthesize $C_3$ through $C_6$ units by utilizing of long-chain fatty acids, and the $C_6$ unit 3HHx is highly plastic because it has one more methylene group than in 3HV, so that it is capable of providing flexibility. Also, the $C_3$ unit 3HP is capable of providing elasticity while maintaining strength.

Accordingly, the use of a microorganism of the genus Aeeromonas according to the present invention makes it possible to produce a wide variety of plastic materials ranging from rigid plastics to elastic plastics by selecting copolymer components and adjusting their composition. Particularly, since 3HHx ($C_6$ unit), which is an important copolymer component, can be synthesized from naturally occurring oils and fats, which are cheap starting materials, the present invention is very advantageous economically.

EXAMPLES

The present invention is hereinafter described in more detail by means of the following examples, which are not to be construed as limitative.

EXAMPLE 1

*Aeromonas caviae* FA-440 (deposited under accession number FERM BP 3432) was subjected to shaking culture at 30° C. for 48 hours using the following medium. Specifically, the medium was prepared by adding water to the following medium composition to make a total quantity of 1 liter (pH 7.0).

| | |
|---|---|
| Meat Extract | 5 g |
| Peptone | 5 g |
| Yeast Extract | 2 g |
| $KH_2PO_4$ | 0.5 g |
| $K_2HPO_4$ | 1.5 g |
| $MgSO_4.H_2O$ | 0.1 g |

After completion of cultivation, the culture broth was centrifuged and bacterial cells were recovered, the entire quantities were transferred into a medium, followed by shaking culture at 30° C. for 24 hours. Specifically, the medium was prepared by adding water to the following medium composition to make a total quantity of 1 liter (pH 7.0).

| | |
|---|---|
| Oleic Acid | 25.4 g |
| $KH_2PO_4$ | 1.5 g |
| $K_2HPO_4$ | 1.5 g |
| $MgSO_4.7H_2O$ | 0.25 g |
| Tween 85 | 0.5 g |

After completion of cultivation, bacterial cells were washed with distilled water and methanol and then dried under reduced pressure to yield dry cells, which were extracted with chloroform at 50° C. for 2 hours. After cell removal, a 10-fold amount of methanol was added to the chloroform extract to precipitate and recover the polyester.

Figure 2:
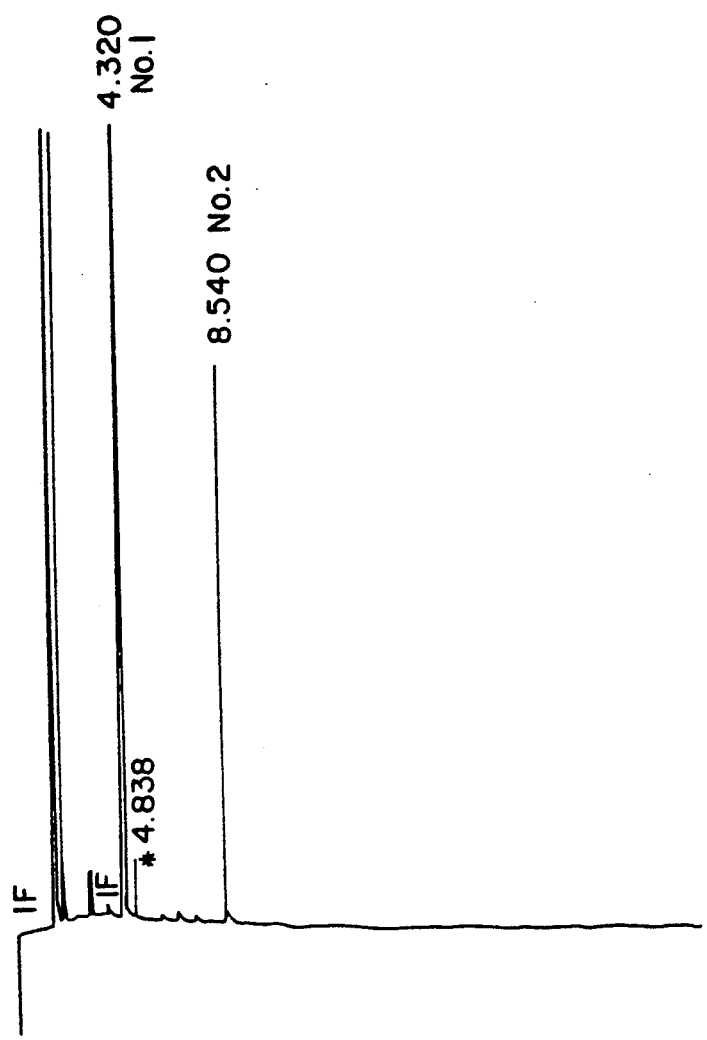
FIG. 2 shows a gas chromatogram of the monomers resulting from methanolysis of the polyester obtained in Example 1.

The resulting polyester was subjected to methanolysis at 100° C. for 140 minutes under acidic conditions with sulfuric acid to convert the monomer into methyl esters, followed by capillary gas chromatographic analysis at increased temperature (FIG. 2).

The capillary gas chromatography was carried out using an HP5890II (produced by Hewlett Packard). The column used therefor is a fused silica capillary column DB-5 produced by J & W, whose inner diameter is 0.25 mm, liquid layer thickness is 0.25 μm, and length is 30 m. The temperature was kept at 60° C. for 3 minutes at the start, increased at a rate of 8° C./min to reach the final temperature of 240° C., and then kept at 240° C. for 3 minutes.

FIG. 1 is a gas chromatogram of the methyl esters of 3-hydroxy fatty acids.

In FIG. 1, No. 1 through No. 6 denote the following:
No. 1: 3-Hydroxypropionate;
No. 2: 3-Hydroxybutyrate;
No. 3: 3-Hydroxyvalerate;
No. 4: 3-Hydroxyhexanoate;
No. 5: 3-Hydroxyoctanoate; and
No. 6: 3-Hydroxydecanoate.

In FIG. 2, No. 1 is the peak for 3-hydroxybutyrate; No. 2 is the peak for 3-hydroxyhexanoate; and * is the peak for crotonic acid derived from 3-hydroxybutyrate by-produced upon hydrolysis of the polyester. As is evident from the comparison of FIGS. 1 and 2, the polyester obtained in Example 1 is a copolymer containing two monomer units of a 3HB (3-hydroxybutyrate) unit and a 3HHx (3-hydroxyhexonoate) unit.

The results are shown in Table 2.

Figure 3:
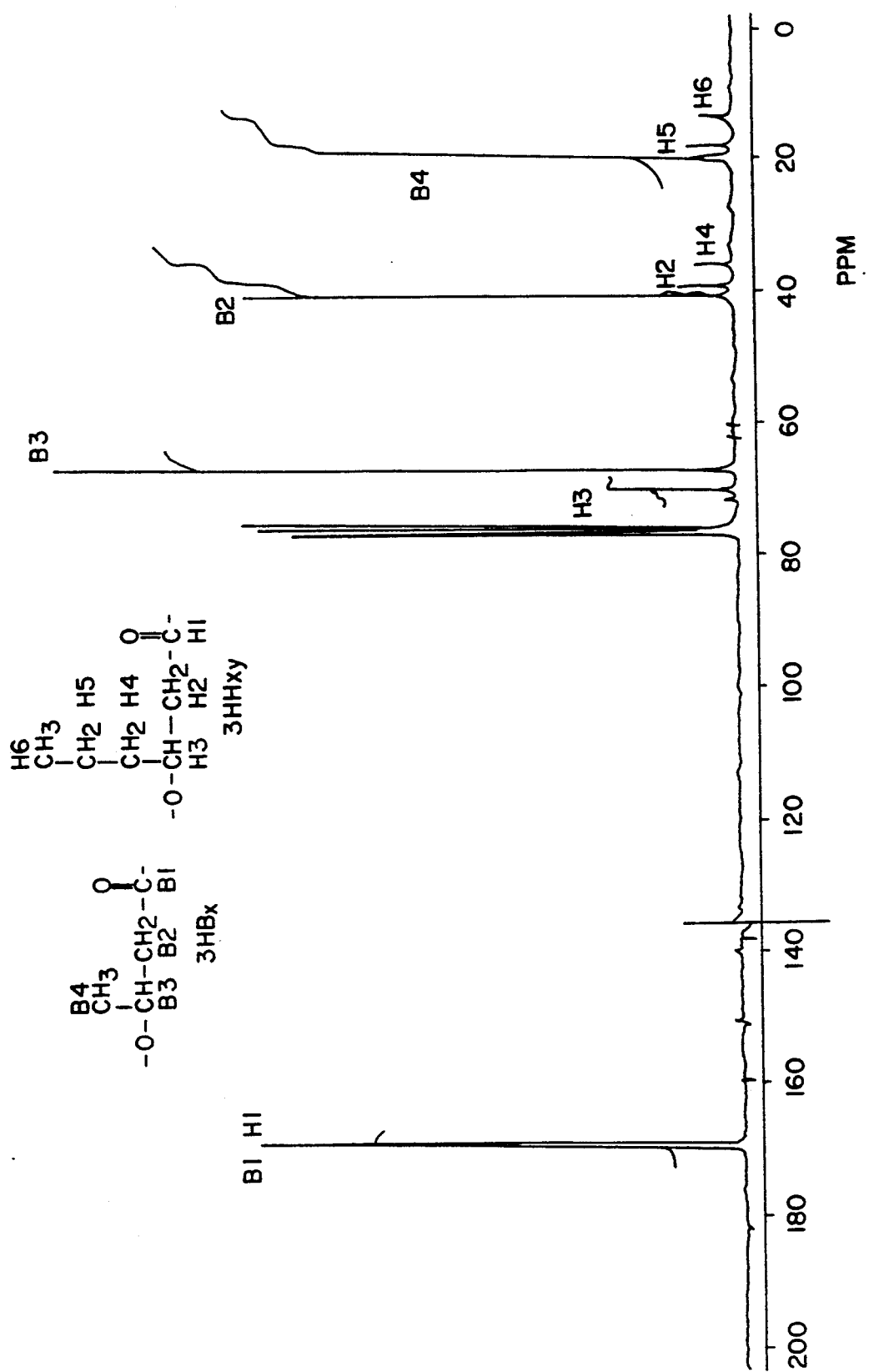
FIG. 3 shows a $^{13}$C-NMR (75 MHz) spectrum of the polyester obtained in Example 1.

The resulting polyester was also subjected to a $^{13}C$-NMR analysis. Its spectrum is shown in FIG. 3, demonstrating that the polyester thus obtained is a copolymer containing two monomer units of 3HB and 3HHx.

TABLE 2

Fermentation Synthesis of Polyester by *Aeromonas caviae* Using Oleic Acid as Carbon Source

| Monomer Unit | Oleic Acid (Carbon Source) Concentration (g/liter) | | | | |
|---|---|---|---|---|---|
| | 1.5 | 2.8 | 8.5 | 17.2 | 25.2 |
| $C_3$ | 0 | 0 | 0 | 0 | 0 |
| $C_4$ | 73 | 77 | 81 | 84 | 85 |
| $C_5$ | 0 | 0 | 0 | 0 | 0 |
| $C_6$ | 27 | 23 | 19 | 16 | 15 |
| $C_7$ | 0 | 0 | 0 | 0 | 0 |
| $C_8$ | 0 | 0 | 0 | 0 | 0 |

When oleic acid was used as the only carbon source, the obtained two-component copolymer had a 3HB($C_4$):3HHx($C_6$) ratio of 85:15.

EXAMPLE 2

The experiment was conducted in the same manner as in Example 1 except that the oleic acid concentration was changed to 1.5, 2.8, 8.5 or 17.2 g/liter. The results are also shown together in Table 2. A two-component copolymer containing $C_4$ and $C_6$ units could be obtained even when the oleic acid concentration was lowered. However, a change in composition took place. Specifically, the $C_6$ unit content increased, while the oleic acid concentration decreased.

EXAMPLE 3

The experiment was conducted in the same manner as in Example 2 except that Aeromonas hydrophila strain OL-338 was used and olive oil as a carbon source was used at a concentration of 2.8, 8.5, 17.2 or 25.4 g/liter. two-component copolymers containing $C_4$ and $C_6$ were obtained. Unlike in Example 2, the content ratio remained almost constant, independent of the olive oil concentration.
3HB($C_4$):3HHx($C_6$)=90:10 to 92:8

EXAMPLE 4

The experiment was conducted in the same manner as in Example 3 except that β-hydroxycaproic acid was used as a carbon source. As a result, the obtained two-component copolymer had a 3HB:3HHx ratio of 51:49.

EXAMPLE 5

The experiment was conducted in the same manner as in Example 3 except that propionic acid was used as a carbon source. As a result, the obtained two-component copolymer had a 3HB:3HP ratio of 45:55.

EXAMPLE 6

The experiment was conducted in the same manner as in Example 3 except that valeric acid was used as a carbon source. As a result, the obtained two-component copolymer had a 3HB:3HV ratio of 2:98, meaning that the copolymer is essentially a P(3HV) homopolymer.

EXAMPLE 7

The experiment was conducted in the same manner as in Example 3 except that 4-hydroxybutyric acid was used as a carbon source. As a result, the obtained two-component copolymer had a 3HB:4HB ratio of 75:25.

EXAMPLE 8

The experiment was conducted in the same manner as in Example 3 except that a corn oil, which is a naturally occurring oil or fat, was used as a carbon source. As a result, the obtained two-component copolymer had a 3HB:3HHx ratio of 85:15.

EXAMPLE 9

The experiment was conducted in the same manner as in Example 3 except that 8 g of oleic acid and 2 g of valeric acid were used as carbon sources. As a result, the obtained three-component copolymer had a 3HB($C_4$):3HV($C_5$):3HHx($C_6$) ratio of 44:48:8.

EXAMPLE 10

The experiment was conducted in the same manner as in Example 3 except that 4.1 g of olive oil and 1.7 g of valeric acid were used as carbon sources. As a result, the obtained three-component copolymer had a 3HB($C_4$):3HV($C_5$):3HHx($C_6$) ratio of 80.2:11.2:8.6.

EXAMPLE 11

The experiment was conducted in the same manner as in Example 3 except that 3.1 g of olive oil and 0.69 g of 4-hydroxybutyric acid were used as carbon sources. As a result, the obtained three-component copolymer had a 3HB:4HB:3HHx ratio of 84.4:7.7:7.9.

EXAMPLE 12

The experiment was conducted in the same manner as in Example 3 except that 0.31 g of olive oil, 0.17 g of valeric acid and 0.69 g of 4-hydroxybutyric acid were used as carbon sources. As a result, the obtained four-component copolymer had a 3HB:4HB:3HV:3HHx ratio of 79.7:8.1:5.4:6.8.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A two-component copolymer consisting of 3-hydroxybutyrate (3HB) units and 3-hydroxyhexanoate (3HHx) units, wherein said units, respectively, have the following structures:

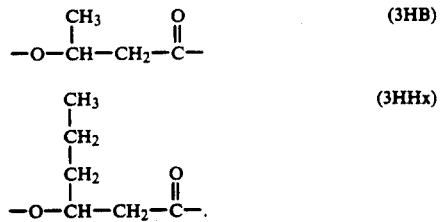

2. A three-component copolymer containing at least a 3-hydroxybutyrate (3HB) unit and a 3-hydroxyhexanoate (3HHx) unit.

3. A four-component copolymer containing at least a 3-hydroxybutyrate (3HB) unit and a 3-hydroxyhexanoate (3HHx) unit.

4. The copolymer according to claim 1, wherein said copolymer contains 50 mol % to 98 mol % of 3-hydroxybutyrate (3HB) units and 50 mol % to 2 mol % of 3-hydroxyhexanoate (3HHx) units.

5. The copolymer according to claim 2, wherein said copolymer contains as a third component a unit selected from the group consisting of a 4-hydroxybutyrate (4HB) unit, a 3-hydroxyvalerate (3HV) unit and a 3- hydroxypropionate (3HP) unit, wherein said units, respectively, have the following structures:

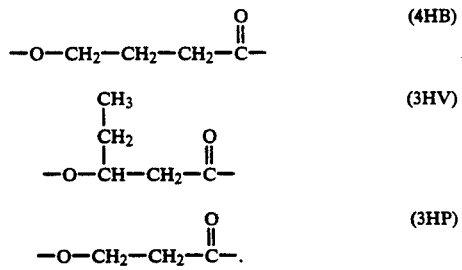

6. The copolymer according to claim 3, wherein said copolymer contains as third and fourth components two units selected from the group consisting of a 4-hydroxybutyrate (4HB) unit, a 3-hydroxyvalerate (3HV) unit and a 3-hydroxypropionate (3HP) unit.

7. *Aeromonas caviae* capable of synthesizing a copolymer containing a 3-hydroxybutyrate (3HB) unit and a 3-hydroxyhexanoate (3HHx) unit.

8. *Aeromonas caviae* capable of synthesizing a three-component copolymer containing at least a 3-hydroxybutyrate (3HB) unit and a 3-hydroxyhexanoate (3HHx) unit.

9. *Aeromonas caviae* capable of synthesizing a four-component copolymer containing at least a 3-hydroxybutyrate (3HB) unit and a 3-hydroxyhexanoate (3HHx) unit.

10. A method for producing a copolymer containing 3-hydroxybutyrate (3HB) units and 3-hydroxyhexanoate (3HHx) units, which comprises:
    culturing a microorganism of the genus Aeromonas in a culture medium under limitation of nutrients other than carbon sources, using as a carbon source a fatty acid having an even number of not less than 6 carbon atoms, a lower alcohol ester thereof, or a naturally occurring oil or fat; and
    recovering said copolymer from the cultured cells.

11. A method for producing a copolymer containing at least one unit selected from the group consisting of a 3-hydroxypropionate (3HP) unit, a 3-hydroxyvalerate (3HV) unit and a 4-hydroxybutyrate (4HB) unit, which comprises:
    culturing a microorganism of the genus Aeromonas in a culture medium under limitation of nutrients other than carbon sources, using as a carbon source 5-chlorovaleric acid or propionic acid, a fatty acid having an odd number of not less than 5 carbon atoms, 4-hydroxybutyric acid, or γ-butyrolactone; and
    recovering said copolymer from the cultured cells.

12. A method for producing a three-component copolymer containing at least a 3-hydroxybutyrate (3HB) unit, a 3-hydroxyhexanoate (3HHx) unit and one unit selected from the group consisting of a 3-hydroxypropionate (3HP) unit, a 3-hydroxyvalerate (3HV) unit, and a 4-hydroxybutyrate (4HB) unit, which comprises:
    culturing a microorganism of the genus Aeromonas in a culture medium under limitation of nutrients other than carbon sources, using as a carbon source a fatty acid having an even number of not less than 6 carbon atoms, a lower alcohol ester thereof, or a naturally occurring oil or fat, and one carbon source selected from the group consisting of 5-chlorovaleric acid or propionic acid, a fatty acid having an odd number of not less than 5 carbon atoms, and 4-hydroxybutyric acid or γ-butyrolactone; and
    recovering said copolymer from the cultured cells.

13. A method for producing a four-component copolymer containing at least a 3-hydroxybutyrate (3HB) unit, a 3-hydroxyhexanoate (3HHx) unit, and two units selected from the group consisting of a 3-hydroxypropionate (3HP) unit, a 3-hydroxyvalerate (3HV) unit, and a 4-hydroxybutyrate (4HB) unit, which comprises:
    culturing a microorganism of the genus Aeromonas in a culture medium under limitation of nutrients other than carbon sources, using as a carbon source a fatty acid having an even number of not less than 6 carbon atoms, a lower alcohol ester thereof, or a naturally occurring oil or fat, and two carbon sources selected from the group consisting of 5-chlorovaleric acid or propionic acid, a fatty acid having an odd number of not less than 5 carbon atoms, and 4-hydroxybutyric acid or γ-butyrolactone; and
    recovering said copolymer from the cultured cells.

14. The method according to any one of claims 10, 12, or 13, wherein said naturally occurring oil or fat is at least one member selected from the group consisting of corn oil, soybean oil, safflower oil, sunflower oil, olive oil, coconut oil, palm oil, rapeseed oil, fish oil, whale oil, lard, and beef tallow.

15. The method according to claim 10, wherein said carbon source is a long-chain fatty acid having an even number of 12 to 22 carbon atoms, and the copolymer P(3HB-CO-3HHx) containing $C_4$ and $C_6$ units is obtained.

16. The method according to claim 12, wherein said carbon source is a mixture of a fatty acid having an odd number of not less than 5 carbon atoms and a fatty acid having an even number of not less than 6 carbon atoms, and wherein a three-component copolymer containing 3HB units, 3HV units, and 3HHx units is obtained.

17. The method according to claim 13, wherein said carbon source is a member selected from the group consisting of olive oil, valeric acid, and 4-hydroxybutyric acid, and a four-component copolymer containing 3HB units, 4HB units, 3HV units, and 3HHx units is obtained.

18. *Aeromonas hydrophila* capable of synthesizing a copolymer containing 3-hydroxybutyrate (3HB) units and 3-hydroxyhexanoate (3HHx) units.

19. The method according to claim 10, wherein said microorganism of the genus Aeromonas is a member selected from the group consisting of *Aeromonas caviae*, strain FA-440, FERM BP 3432, and *Aeromonas hydrophila*, strain OL-338.

20. The method according to claim 10, wherein said nutrients other than carbon sources are selected from the group consisting of phosphorus, minerals, and vitamins.

21. The method according to claim 20, wherein said culturing under nitrogen limitation is carried out in a first stage wherein said Aeromonas is cultured under nutrient-rich conditions, followed by a second stage wherein the Aeromonas cells are washed and recovered, after which they are cultured in a medium containing a newly added carbon source which determines the structure of the synthesized polyester, in which the nitrogen source is limited such that the C/N ratio is not less than 7.

22. The method according to claim 21, wherein no nitrogen source is present during the second stage of culturing.

* * * * *